(12) United States Patent
Moser et al.

(10) Patent No.: US 9,022,994 B2
(45) Date of Patent: May 5, 2015

(54) INJECTION DEVICE WITH A VARIABLE THREAD GUIDE

(75) Inventors: Ulrich Moser, Heimiswil (CH);
Christian Schrul, Burgdorf (CH);
Markus Tschirren, Kirchberg (CH);
Juerg Hirschel, Aarau (CH)

(73) Assignee: TeePharma Licensing AG, Burgdorf (CH)

( * ) Notice: Subject to any disclaimer, the term of this patent is extended or adjusted under 35 U.S.C. 154(b) by 130 days.

(21) Appl. No.: 11/837,845

(22) Filed: Aug. 13, 2007

(65) Prior Publication Data
US 2008/0108953 A1     May 8, 2008

(30) Foreign Application Priority Data
Aug. 14, 2006   (DE) .......................... 10 2006 038 103

(51) Int. Cl.
*A61M 5/315*     (2006.01)
*A61M 5/20*      (2006.01)
*A61M 5/24*      (2006.01)
*A61M 5/31*      (2006.01)

(52) U.S. Cl.
CPC ............. *A61M 5/31583* (2013.01); *A61M 5/20* (2013.01); *A61M 5/2448* (2013.01); *A61M 5/3146* (2013.01); *A61M 5/31501* (2013.01); *A61M 5/31511* (2013.01); *A61M 5/31541* (2013.01); *A61M 5/31553* (2013.01); *A61M 5/3156* (2013.01); *A61M 5/31568* (2013.01); *A61M 5/31595* (2013.01); *A61M 2005/3125* (2013.01)

(58) Field of Classification Search
CPC ...................... A61M 5/31511; A61M 5/31501; A61M 5/315; A61M 5/31528; A61M 5/31525; A61M 5/31533; A61M 5/31535; A61M 5/31548; A61M 5/3155; A61M 5/31551; A61M 5/31578; A61M 5/3158; A61M 5/31583
USPC .................................................. 604/218, 224
See application file for complete search history.

(56) References Cited

U.S. PATENT DOCUMENTS

| | | | | |
|---|---|---|---|---|
| 3,353,718 A | * | 11/1967 | McLay ......................... | 222/158 |
| 5,092,842 A | | 3/1992 | Bechtold et al. | |
| 5,112,317 A | * | 5/1992 | Michel ......................... | 604/208 |
| 5,378,233 A | | 1/1995 | Haber et al. | |
| 5,383,865 A | | 1/1995 | Michel | |
| 5,647,856 A | * | 7/1997 | Eykmann et al. .............. | 604/181 |
| 6,004,298 A | * | 12/1999 | Levander ....................... | 604/211 |
| 6,048,336 A | * | 4/2000 | Gabriel ......................... | 604/211 |

(Continued)

FOREIGN PATENT DOCUMENTS

| | | |
|---|---|---|
| DE | 635934 C1 | 10/1936 |
| DE | 198 21 934 | 11/1999 |

(Continued)

*Primary Examiner* — Aarti B Berdichevsky
*Assistant Examiner* — Laura Schell
(74) *Attorney, Agent, or Firm* — Dorsey & Whitney LLP

(57) ABSTRACT

An injection device for injecting a substance from an ampoule inserted in the device, the device including one or more of the following components: an internal thread for engaging a threaded rod, the internal thread including several contact faces enabling the use of a different threaded rods, a real-time display for displaying a quantity of a substance, e.g., the quantity to be injected or dispensed, the quantity available for dispensing or the quantity dispensed, a mechanical lock for locking the device prior to inserting the ampoule, and a claw lock for preventing use of the injection device.

26 Claims, 15 Drawing Sheets

(56) References Cited

U.S. PATENT DOCUMENTS

| | | |
|---|---|---|
| 6,793,646 B1 | 9/2004 | Giambattista et al. |
| 2004/0186431 A1 | 9/2004 | Graf et al. |
| 2004/0186443 A1* | 9/2004 | Covino et al. .............. 604/242 |
| 2005/0065477 A1 | 3/2005 | Jost |
| 2005/0137571 A1 | 6/2005 | Hommann |
| 2005/0154351 A1 | 7/2005 | Graf et al. |
| 2005/0222540 A1 | 10/2005 | Kirchhofer |
| 2005/0261634 A1 | 11/2005 | Karlsson |

FOREIGN PATENT DOCUMENTS

| | | |
|---|---|---|
| DE | 69721700 T2 | 3/2004 |
| DE | 69922027 T2 | 10/2005 |
| DE | 10 2004 055 298 | 5/2006 |
| DE | 60302335 T2 | 8/2006 |
| EP | 0 554 995 | 8/1993 |
| EP | 0 937 471 | 8/1999 |
| WO | WO 00/41752 | 7/2000 |
| WO | WO 00/62839 | 10/2000 |
| WO | WO 01/72361 | 10/2001 |
| WO | WO 02/092153 | 11/2002 |
| WO | WO 03/000317 | 1/2003 |
| WO | WO 03/053499 | 7/2003 |
| WO | WO 2004/006997 | 1/2004 |
| WO | WO 2005/072796 | 8/2005 |
| WO | WO 2007/082400 | 7/2007 |

* cited by examiner

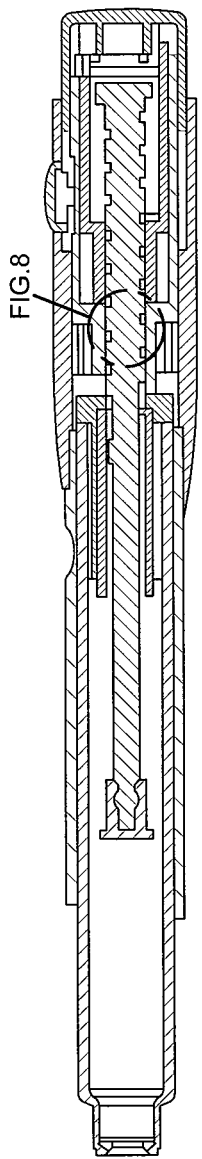
FIG. 7
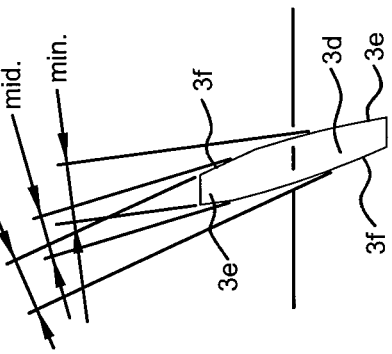
FIG. 9
FIG. 8

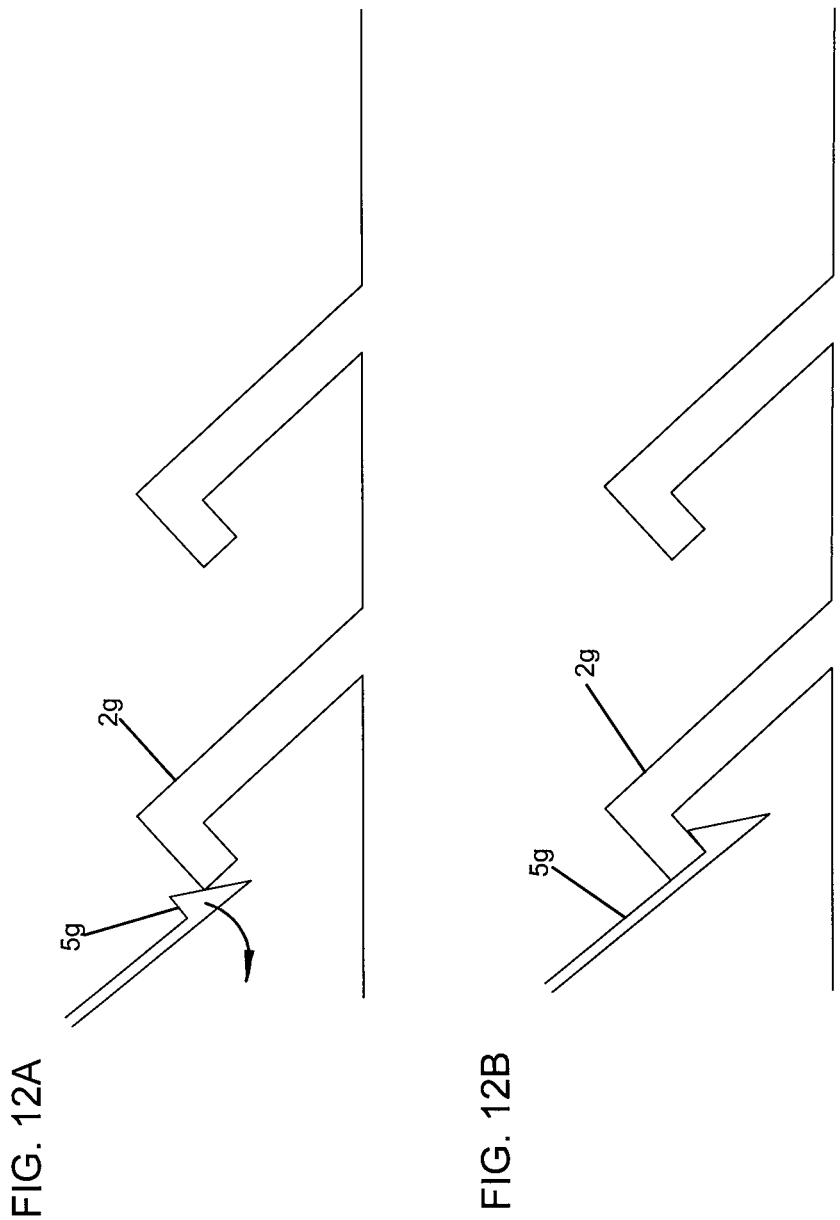

INJECTION DEVICE WITH A VARIABLE THREAD GUIDE

CROSS-REFERENCE TO RELATED APPLICATIONS

This application claims priority to German Patent Application No. DE 10 2006 038 103.3 filed on Aug. 14, 2006, the contents of which is incorporated in its entirety herein by reference.

BACKGROUND

The present invention relates to devices for injecting, dispensing, administering, delivering or infusing substances, and to methods of making and using such devices. More particularly, the present invention relates to such devices comprising one or more of the following components or features: a rod or rod-like member which may be threaded and thought of or referred to as a plunger rod; a real-time display for displaying various quantities of a substance, e.g., the quantity to be injected or dispensed, the quantity available for dispensing, the quantity dispensed, etc.; a mechanical lock for use prior to mixing an ampoule, possibly a 2-chamber ampoule; a guide for the rod or rod-like member; and a claw lock.

In some embodiments of injection devices, to set or select the quantity of a substance to dispensed, a setting movement is performed on a setting element. The setting element may be a dose setting knob or a dose setting ring and the setting movement may be a rotating or turning movement of the knob or ring wherein the extent of the rotation, in other words, a rotation or rotational angle, defines what quantity of substance will be dispensed from the injection device in an injection operation. In the case of injection devices designed to dispense a fixed and possibly pre-set quantity of a substance, for example, fixed-dose injection pens, the setting movement may be effected to prime the device for dispensing a pre-defined dose.

SUMMARY

One object of the present invention is to provide for the robust and simple setting or selection of a dose or quantity of a substance to be injected or delivered from an injection device.

In one embodiment, the present invention comprises a rod or rod-like member for use in an injection device. In some embodiments, the rod or rod-like member is threaded and designed to be able to assume predefined fixed rotated positions. Catch elements associated with the device are able to engage with the threaded rod and thus establish a coupling between the threaded rod and the injection device or with a setting element of the device. The catch elements may comprise snapper or engagement elements pre-tensioned elastically and/or radially inwardly or outwardly. In some embodiments, the threaded rod has longitudinally extending engagement regions, grooves or channels which interrupt the thread on the external face of the rod so that it assumes a cross-section in the form of a star, for example, with three, four or alternatively more than four, for example five or six, points and/or webs.

In one embodiment, a sturdy, easy-to-sense and simple setting of a predefined fixed dose is enabled by providing a threaded rod of a cruciform design with four points, for example. The rod can be rotated into only four defined and stable rotated positions. In the stable rotated positions, one or more engaging elements which are suitably arranged around the rod depending on its shape engage in the grooves or webs between the points and hold the rod in one of the positions. Rotating the threaded rod by only 90°, 180°, 270° and other multiples of 90° causes the threaded rod to assume stable and defined rotated positions.

In some embodiments, the threaded rod may be designed so that at least in the region of the grooves or axially or longitudinally extending engagement regions, the outer or peripheral regions of the threaded rod are provided with a slight chamfer. Thus, the engaging elements, which are radially pre-tensioned toward the rod and advantageously permit a rotation of the rod in one direction due to a sliding movement across the chamfered regions and block a rotation in the locking or opposite direction by engaging in the engagement regions, can be easily disengaged when the threaded rod is rotated opposite the locking direction and are pushed out of or can be pushed out of the engagement regions so that they are guided across the chamfered outer regions into the adjacent engagement region. Providing a chamfer at the outer regions means that a point or web of the threaded rod between two grooves or engagement regions has a higher and a lower face, in which case the higher face is disposed on the side from which the engagement element no longer has to be pushed out to move across the chamfered outer region so that the rotation of the threaded rod can be blocked by the engagement element. The smaller face, on the other hand, makes it easier to turn the threaded rod further because the engagement element only has to be pushed along the smaller face to the chamfered region to permit a rotation of the threaded rod. In some embodiments, the engagement elements may be provided with a ramp, which is of a design matching the ramp of the peripheral region of the threaded rod, for example, and which facilitates or enables an outward pushing movement of the engagement element due to a rotating movement in a releasing direction.

In some embodiments, the threaded rod has a wider portion at the proximal or rear end, such as a circumferentially extending ring or radially projecting web or area, from which at least one engagement element projects in the distal or forward direction. The at least one engagement element may take the form of one or more webs, for example, suitable to engage and/or lock with matching co-operating elements after the threaded rod has been fully pushed in. The engagement of the complementary or co-operating elements blocks any further rotating movement of the threaded rod or the dose setting element relative to the injection device and the injection device can therefore no longer be used.

In another embodiment, the present invention comprises an injection device comprising a rod or rod-like element as described above.

In some embodiments, a dose setting element is advantageously provided on the injection device, such as a dose setting knob or a rotating knob for example, which may be connected to other elements such as a rotating sleeve or rotating element, for example. The dose to be dispensed can be set by the dose setting element, and/or the injection device may be primed and the dose set. In some preferred embodiments, a rotating movement of the dose setting element tautens a spring element such as a torsion spring for example, which stores the energy for the subsequent injection and forward drive of the threaded rod and releases it when a trigger element is operated. A rotating sleeve connected to the dose setting element and/or the dose setting element itself has at least one and, in some embodiments, at least two engagement elements lying opposite one another and pre-tensioned radially inwardly for example. The engagement elements are able to engage in co-operating engagement regions of the threaded rod and permit a rotating movement of the threaded rod relative to the rotating sleeve or to the dose setting element in one direction. When the rotating sleeve or the dose setting element is rotated in the opposite direction, the engagement elements remain engaged with the threaded rod and drive it with them so that the energy stored in the torsion spring due to the setting movement can be converted into a rotating movement of the threaded rod.

In some embodiments, at least one engagement element pre-tensioned radially outwardly is also provided on the rotating sleeve or dose setting element, and is able to engage in a window or a groove or recess of the injection device for example, thereby holding or locking the rotating sleeve or the dose setting element in a predefined rotated position after setting the dose or priming the injection device. The element used for locking purposes may be released again by a release button for example, and when the release button is operated, the engagement element pre-tensioned radially outwardly is pushed back in a direction oriented radially inwardly for example, so that the rotating sleeve or the dose setting element is no longer coupled with the injection device and a rotating movement is possible.

In some embodiments, integrated as part of the injection device, fixedly connected to the injection device or provided as a separate element, the injection device comprises at least one guide element, which has an elastic retaining element which is pre-tensioned radially inwardly for example. The guide element is able to engage in at least one engagement region of the threaded rod to permit a rotating movement of the threaded rod in one direction relative to the injection device and block it in the other direction. The guide element also has an internal thread, which may also comprise one or more partial thread segments. This internal thread or the partial thread segments may be designed so that they have several contact faces, as is the case with the thread illustrated in accompanying FIG. 9 for example, thereby permitting a thread engagement for threads of different pitches. For example, the thread segments may be designed so that different threaded rods with a different external thread of a different pitch can be reliably guided between a minimum pitch defined by first contact faces of the internal thread and by a maximum pitch defined by second faces of the internal thread. This, for example, makes it possible to set different doses by the same rotating movement depending on the substance to be administered by using threaded rods with an external thread of a different pitch.

In some embodiments, the injection device has engagement elements or claws to establish a claw coupling with co-operating engagement elements or claws of the threaded rod. The engagement elements of the injection device may be provided on a surface of a rotating sleeve pointing in the proximal direction, a guide sleeve or the injection device itself.

By virtue of another aspect of the present invention, the invention comprises an injection device with a transmission element, which is coupled with a dispensing element such as a plunger rod or a threaded rod of the injection device and which can be coupled with a display element for use with an ampoule which can be inserted in the injection device.

When using injection devices, it is of advantage to provide a display, on which data relating to the doses already administered or doses still contained in the injection device or about the current dispensing operation can be read. However, problems can occur if this display is not functioning correctly because a user might wrongly assume that the injection device contains a bigger quantity of substance than is actually the case.

Therefore, one objective of the present invention is to provide a display, and an injection device comprising the display, which permits a reliable display of a quantity of substance or dose.

In one embodiment, display element in accordance with the present invention for displaying an administering parameter, such as a quantity of a substance still contained in an injection device or already dispensed from an ampoule inserted in the injection device, is coupled as far as possible directly with a dispensing element of the injection device, for example with a plunger rod or threaded rod which drives a stopper into an ampoule or into a reservoir. Coupling the display element as far as possible directly with the drive element means that there are no or few intermediate elements which can cause errors or are susceptible to errors. This enables a robust and reliable display to be provided directly, which may be used to display a remaining quantity or as a real-time display. In terms of administering parameters, the display element may also display the administering or dispensing time, thereby enabling a user to check the dispensing time, or the dispensing time may be stored and used for evaluation purposes, for example.

In some preferred embodiments, the display element is connected to the dispensing element directly, in which case it is connected to it so that it is not able to move or rotate relative to it, and has a marking on an external face in the circumferential direction and/or longitudinal direction for displaying the dose, which can be read through a window or by a marking past which the display element can be moved by sliding or rotating it.

Alternatively, the display element may be coupled with the driving or dispensing element, in other words not directly connected to it, in which case the coupling is achieved by a thread engagement or other movement or a force-transmitting mechanism, such as a screw, a gear, a gear mechanism, link, etc. For example, the display element may have a thread and, if the display element is provided in the form of a sleeve, an internal thread, which engages in an external thread of a plunger rod or threaded rod so that the display element mounted in the injection device cannot move axially but can be rotated. Thus, the display element is rotated directly by rotating or displacing the threaded rod or plunger rod and, on rotation, a reading can be taken from printed information on the external face of the display element about the dose that was dispensed or is still available in conjunction with a scale which does not rotate. In the situation where a thread engagement is used, the thread is advantageously of a design that is not retained by friction so that the display element can simply be rotated and the display element does not obstruct a dose priming or dispensing movement.

In some embodiments, the display element may advantageously be provided not on an injection device but on an ampoule which is inserted in the injection device, which is not coupled with a coupling element of the injection device until or after it is fitted in the injection device, and a movement of a stopper of the ampoule can be converted into a corresponding movement of the display element, thereby providing a real-time display.

By virtue of another aspect of the present invention, the invention comprises an injection device with a display element of the type outlined above.

In some embodiments, the injection device advantageously has at least one orifice, for example a viewing window, where a reading can be taken from a marking of the display element on an external face of the display element fitted in the injection device.

To mount the display element so that it can not be displaced in translation but is able to rotate, an annular groove or an annular web may be provided on the injection device for example, in which a matching co-operating element such as an annular web or an annular groove of the display element engages.

The injection device may be designed so that the display element can be moved inside the injection device, for example when an ampoule is fitted, in which case the display of the display element can not be read from a window when no ampoule is fitted and a colour code on the peripheral face of the display element indicates that there is no ampoule fitted. It is only when or after an ampoule is inserted due to an ampoule inserting operation, for example, that the display element is moved relative to a reading position, for example a viewing window, that the display or print on the display element becomes visible. The display element may be disposed entirely or only partially inside the ampoule.

By virtue of another aspect, the present invention relates to a method of securing a mechanism, e.g., securing a setting mechanism or a setting element of an injection device to prevent it from being operated. In one embodiment, the invention comprises an operating or anti-rotation lock to prevent the setting element from being rotated, in which case the lock can be released by inserting an ampoule in the injection device.

If an injection device is used in which an ampoule must be inserted in the injection device before it can be used, such as a 2-chamber ampoule which must be inserted and mixed directly before use, problems can occur if a user of the injection device proceeds with a setting or operating procedure before inserting the ampoule.

Thus, another object of the present invention is to provide a mechanical lock and an injection device incorporating such a mechanical lock which increases reliability during the operating sequence of an injection device in which an ampoule has to be inserted.

In one embodiment, an injection device in accordance with the present invention has a housing and an operating element mounted in the housing or connected to or coupled with the housing. For the purpose of the invention, the operating element, which might be a setting knob, a knob which has to be depressed or a rotating knob, is mounted in the housing or coupled with or connected to the housing so that the operating element is held by a first retaining connection in a first position by reference to the housing of the injection device, for example is prevented from being moved axially. This being the case, the retaining connection is designed so that it is released as or after an ampoule is fitted or inserted or pushed in so that the operating element is moved into a second retaining position which is axially offset from the first retaining position in the proximal direction, where it is retained by a second retaining connection. In some embodiments, the operating element is moved relative to the housing of the injection device when the ampoule is fitted or pushed in, in other words is pushed out of the injection device in the proximal direction. However, the injection device may be designed so that a coupling or a coupling element is provided, which is moved when the ampoule is inserted so that it moves into abutment with a proximal ampoule edge and thus releases the operating element. This being the case, the actual operating element may remain stationary relative to the injection device or may also be moved.

In some preferred embodiments, the operating element or coupling element is mounted in the injection device so that it is not moved out of the first retaining connection into the second retaining connection until after the ampoule has been fully inserted or pushed in or screwed in, which can cause the two substances contained in the ampoule to be mixed at the same time. For example, the operating or coupling element may be disposed in the injection device in such a way that an ampoule which has to be fitted or pushed in by a previously known degree or dimension, for example, does not come into contact with the coupling or operating element until the last part of the insertion distance. Thus, the ampoule can be screwed into the injection device before this last distance without contacting or moving the coupling or operating element and it is not until the ampoule makes contact with the coupling or operating element and the movement caused by fully inserting the ampoule that the coupling element releases the mechanism for operating the injection device or the operating element is released for operation and to enable a user to make a setting by extracting it out of the housing of the injection device.

The first and/or second retaining connection may be provided in the form of a catch connection, for example, in which case a catch ring may be provided, which projects radially or outwardly from a coupling or operating element and establishes a first retaining connection in conjunction with an annular groove of the injection device or housing and the second retaining connection is established by another annular groove of the injection device or the housing. The retaining element may also be provided in the form of other mechanical couplings, which can be released when a defined minimum force acts on this coupling.

The mechanical lock may be such, for example, that an anti-rotation lock is provided for the setting element by guiding grooves projecting from the setting element so that the setting element is prevented from rotating in a distal position. Once an ampoule is screwed in, the locked setting element is pushed so far in the proximal direction that the grooves used to establish the anti-rotation lock are pushed out of the elements of the injection device or housing which retain and guide these grooves, for example, thereby enabling the setting element to be rotated and thus operated. Another option is to provide a coupling element which does not enable the setting element to be rotated until after a movement in the proximal direction. For example, this coupling element may be of an annular design and may have inwardly and outwardly directed webs, which engage in grooves of the setting element and grooves of the injection device or housing, thereby preventing the setting element from being rotated relative to the housing of the injection device. When the setting element is moved in the distal direction against the force of a spring pre-tensioning the coupling element in the distal direction via an ampoule inserted in the injection device and screwed in, for example, so that the webs of the coupling element are pushed out of the grooves of the setting element and/or out of the grooves of the injection device, the coupling of the setting mechanism with the injection device is released and the injection device can then be operated, e.g., when the ampoule has been fully inserted in the injection device.

When manufacturing injection devices, e.g., injection devices designed to administer a fixed dose of a substance, their construction and the dose setting mechanism may be configured for a specific application. For example, to dispense a large quantity of substance or to produce a long stroke of the setting element, an internal thread of the injection device in which a threaded rod or setting element is guided is provided with a large pitch. If an existing injection device also has to be used for dispensing smaller doses of substances, it is necessary to come up with a new design and produce this new design to provide an internal thread with a smaller pitch, for example. Therefore, another object of the present invention is to provide an injection device which can be used universally.

In some embodiments, an injection device in accordance with the present invention has an internal thread for guiding a threaded rod or setting element, for example, and the internal thread is designed so that it has several contact faces to enable different threaded rods with an external thread of a different pitch to be guided without having to replace or modify the internal thread of the injection device. Accordingly, in some preferred embodiments, the internal thread is made up of individual thread portions. These thread portions may be offset from one another in the circumferential direction and may extend across 1/Nth of the circumference, for example, where N represents a natural number. For example, the thread portions are such that they extend across a half or a third or a quarter of the circumference on the internal face of the injection device or a housing thereof. in some embodiments, the individual thread portions have at least two contact faces on which threads of a different pitch can be guided.

In some preferred embodiments, the thread portions have at least four side faces in which a thread can be guided, in which case two side faces are disposed parallel with one another respectively. In the circumferential direction, i.e. along the course of a thread segment or thread part-element, the contact surfaces for guiding the different threads alternate indirectly or directly. For example, the contact surfaces may either contact one another directly or be used by thread portion segments or thread portion part-pieces which are used to guide other threads of a different pitch.

It may be that such a thread or thread part-piece is designed so that more than two threads of a different pitch can be guided. To this end, the thread or thread segment contact faces may have a minimum pitch and a maximum pitch predefined by the thread segments for guiding threaded rods with a variable pitch. Another option is one where the thread segments have several contact faces and are disposed in the circumferential direction so that only threads of defined pitches can be guided, for example three different predefined pitches.

Generally speaking, depending on the design of a thread segment, e.g., the design of the contact faces of the thread segment, and depending on the distribution of the thread segments in the circumferential direction, it is possible to predefine which external threads can be guided by thread segments with one or more such internal threads of differing pitch.

In accordance with the present invention, therefore, it is possible for a single injection device or a single internal thread of the invention to guide elements with an external thread of a different pitch without having to modify the structure of the internal thread or the injection device. Consequently, the same injection device can be used for different applications which, for example, require short or also long strokes to set a dose.

When a substance contained in an ampoule in an injection device has been fully or partially dispensed, for which purpose a threaded rod or plunger rod pushes on a stopper to force the substance by moving the stopper inside the ampoule, for example, it may be that this plunger rod or threaded rod is inadvertently pulled back inside the injection device, which can lead to incorrect operation of the injection device. Therefore, another object of the present invention is to provide a threaded rod and an injection device incorporating such a threaded rod, which ensures that the threaded rods can no longer be pulled out once they have been fully pushed in.

Thus, in some embodiments, a threaded rod in accordance with the present invention has an anti-rotation locking element, e.g., a claw lock, which is disposed on the threaded rod at or adjacent to its proximal end so that the anti-rotation lock or claws can be pushed into co-operating elements retaining or engaging in the locking elements or claws when the threaded rod or plunger rod has been pushed as far as a predefined distal end position of the injection device, for example. This being the case, the claws or rotation locking elements in which the claws or rotation locking elements of the threaded rod engage are permanently connected to the injection device or a part of it, for example, a part of the housing of the injection device. A threaded rod pushed into the injection device can therefore no longer be rotated once the claws or locking elements have been pushed into the co-operating locking elements of the injection device because of the engagement between the elements. The engagement might be based on webs projecting into grooves for example, and the threaded rod or plunger rod is coupled with the injection device so that it can not rotate, thereby making it impossible to turn it. A threaded rod can therefore be retained in an inserted end position because the claw lock ensures that turning is no longer possible and an axial movement is prevented by the thread coupling.

Accordingly, if using the threaded rod in accordance with the present invention, it is not absolutely necessary to provide any other retaining mechanism in the injection device for holding and securing the threaded rod in the end position. The threaded rod is already fixed by the threaded rod design in accordance with the invention and the claw lock provided or disposed on it.

In some embodiments, the rotation locking elements of the injection device may be provided in the form of indentations in or claws on the injection device or parts of the injection device, such as the rotating sleeve. Various designs of co-operating elements of the injection device are possible, and the rotation locking co-operating elements may be such that they establish a positive connection with the rotation locking elements of the threaded rod engaging in or pushed into the rotation locking co-operating elements, so that the positive connection thus prevents the threaded rod from being turned in the proximal and/or distal direction. The rotation locking elements on the threaded rod may be resiliently mounted, for example, so that they are able to snap or latch in the rotation locking co-operating elements of the injection device in the distal end position for example. The rotation locking elements of the threaded rod may also be fixedly mounted and may be at least slightly or partially deformable so that they are able to snap or latch in the rotation locking co-operating elements of the injection device in the distal end position. When the rotation locking elements snap or latch into the rotation locking co-operating elements, they are positively connected to the rotation locking co-operating elements, thereby preventing any movement or rotation of the threaded rod in the proximal and/or distal direction.

BRIEF DESCRIPTION OF THE DRAWINGS

FIG. 7 is a view in cross-section showing an injection device without an ampoule inserted;

FIG. 8 shows detail A from FIG. 7 and illustrates the threaded engagement of the guide sleeve in the threaded rod;

FIG. 9 shows the thread of the guide sleeve illustrated in FIG. 8 with different contact faces for guiding different threaded rods with an external thread of a different pitch;

FIGS. 12A-12B show an embodiment of a claw lock in accordance with the present invention.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to an electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figure 1:
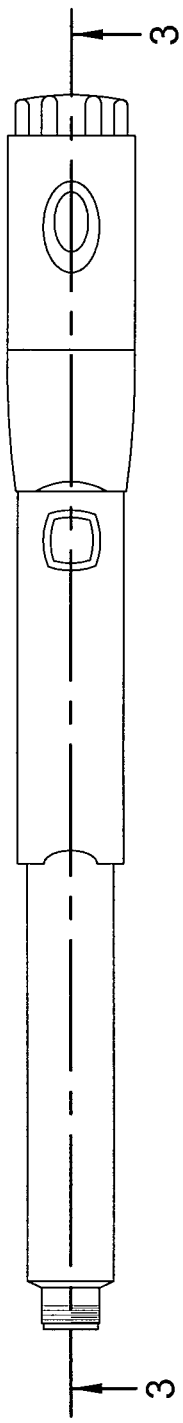
FIG. 1 is a plan view of an embodiment of an injection device in accordance with the present invention.
Figure 3:
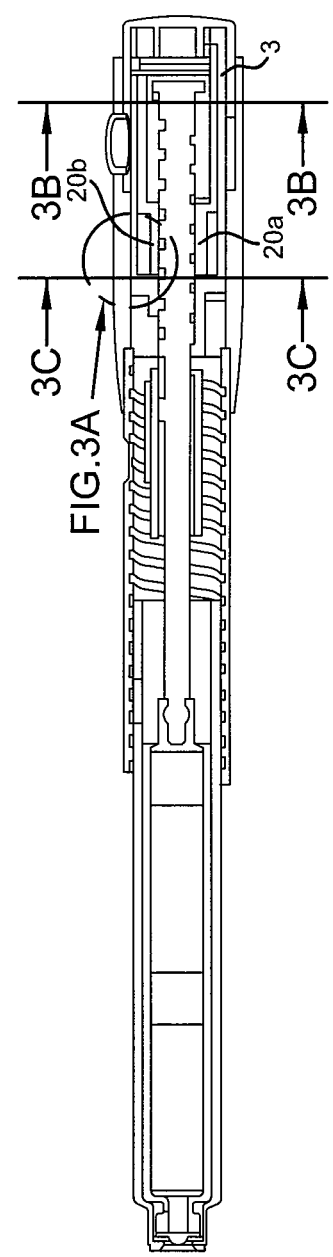
FIG. 3 is a sectional view showing an alternative embodiment along section A-A indicated in FIG. 1 together with other sections B-B and C-C indicated in the first view in section.

FIG. 1 illustrates an embodiment of a fixed-dose injection device, i.e., an injection pen, in which the dose to be dispensed is set using the dose setting knob 1.

The pen has a threaded rod 5, which is designed in the shape of a star with four points 5b, as illustrated by the sections shown in FIGS. 3 to 6, thereby providing a simple and robust means of setting the fixed dose.

In principle, the threaded rod 5 may have a star-shaped cross-section (Swiss cross) but the star may also have more or less points 5b than the Swiss cross.

Figure 2:
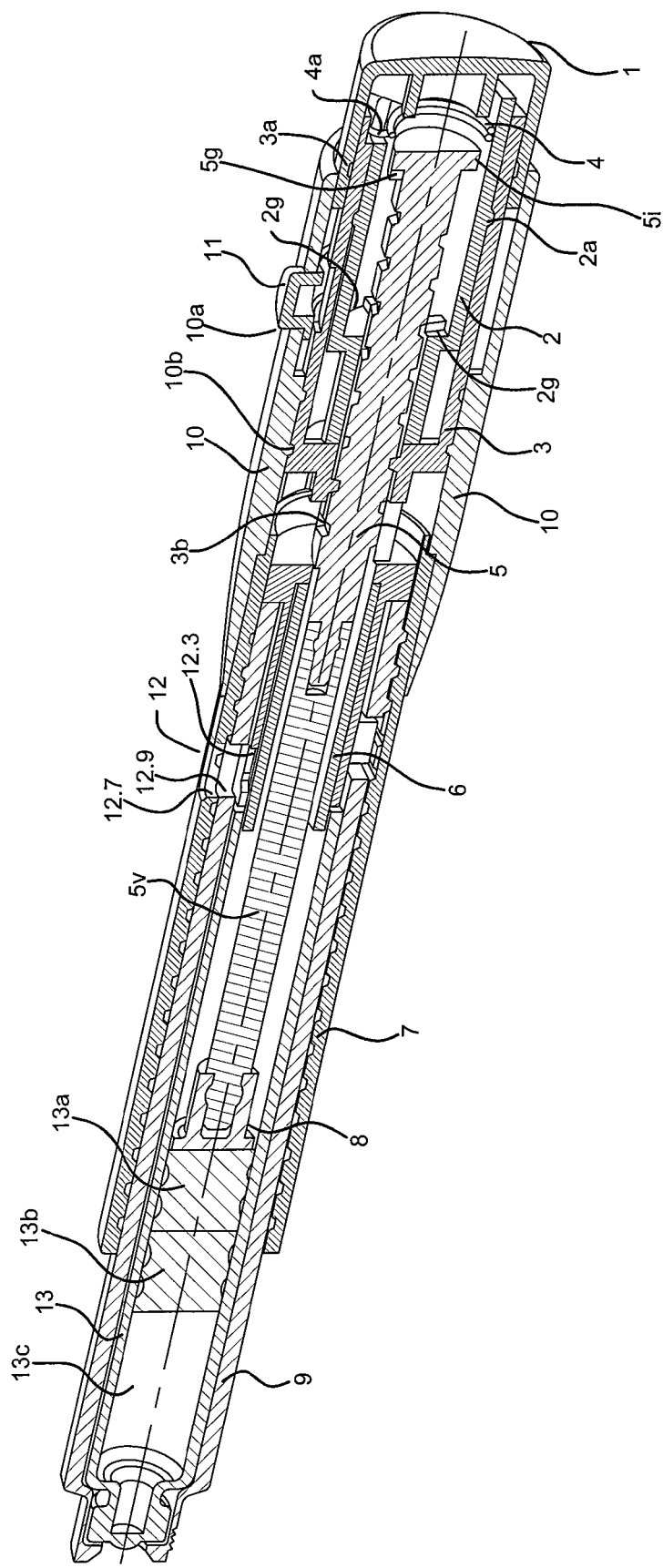
FIG. 2 is a perspective view of the injection device in cross-section along section A-A indicated in FIG. 1.
Figure 3B:
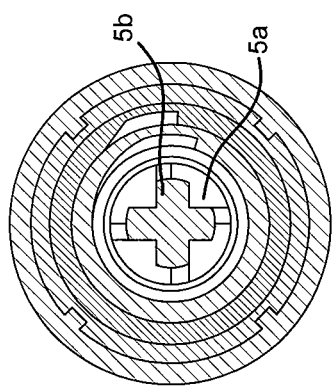
Figure 3C:
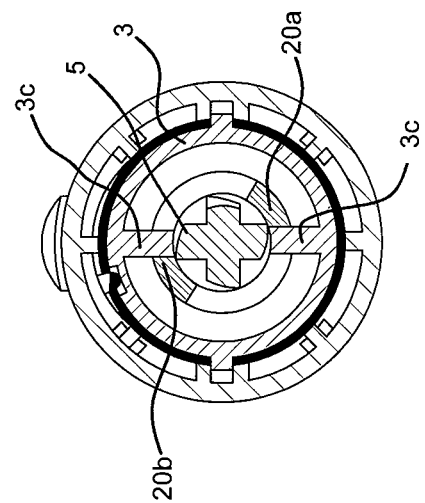
Figure 3A:
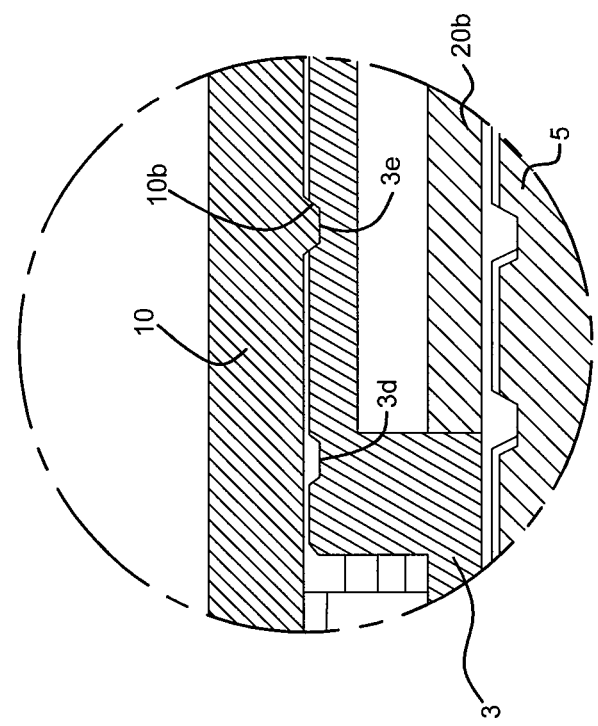
Figure 4:
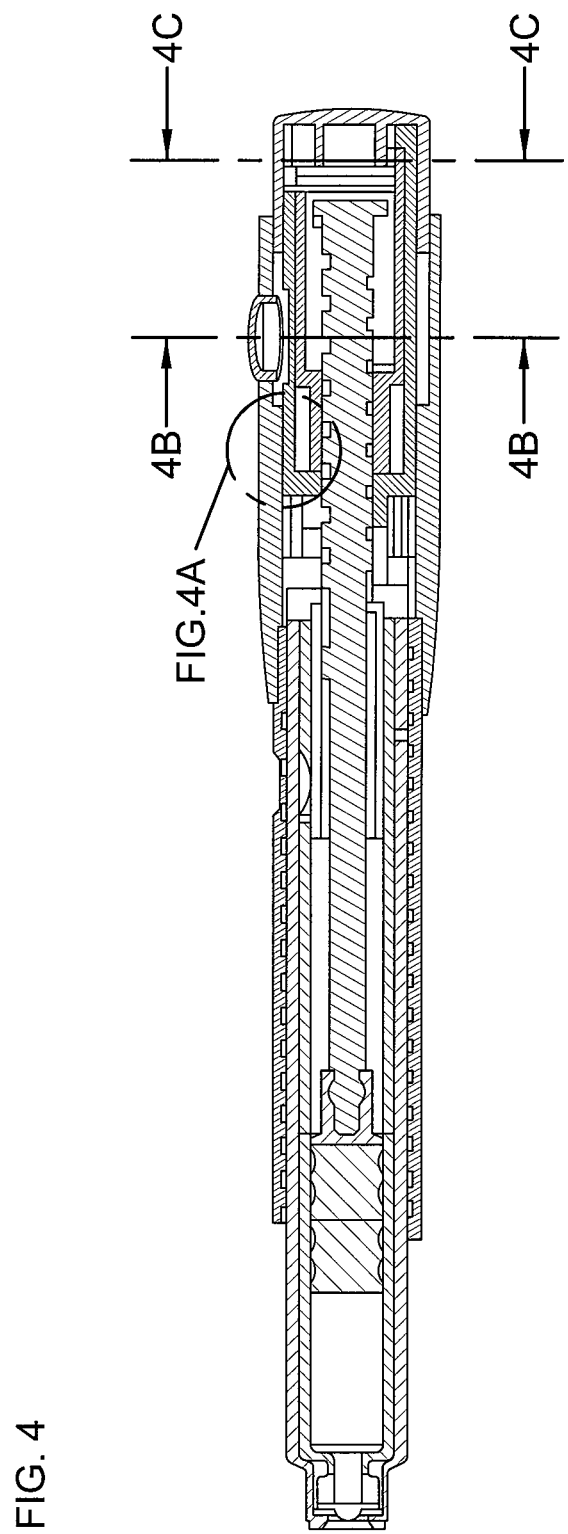
FIG. 4 shows the injection device illustrated in FIG. 3 after mixing and with the mechanism extracted.
Figure 4A:
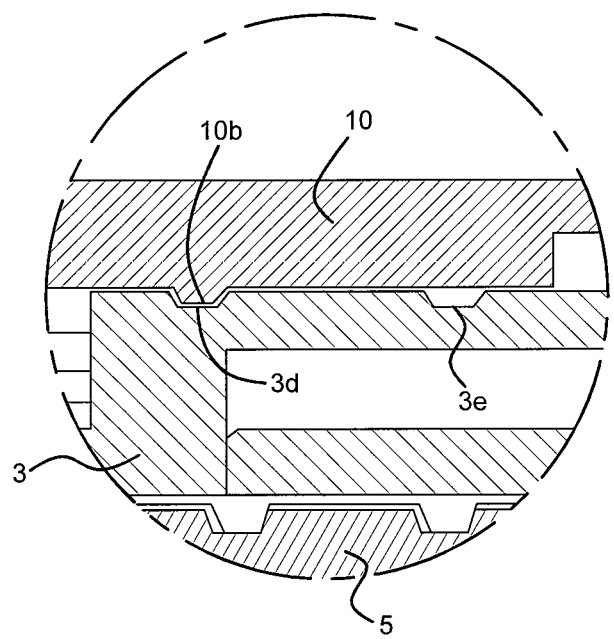
Figure 4B:
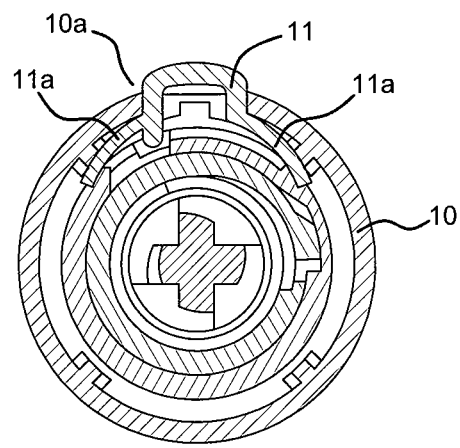
Figure 4C:
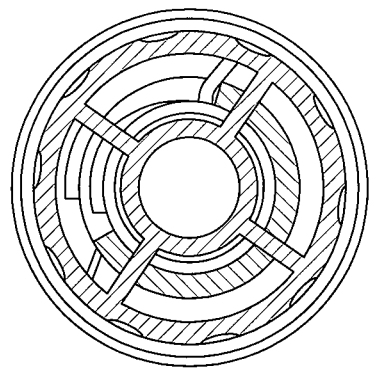

FIG. 2 illustrates the pen shown in a perspective view in FIG. 1 but in section along line A-A.

The guide sleeve 3 may be connected to the housing 10 and is mounted or carried so that it can not rotate relative to the housing 10. Inside the guide sleeve 3 is a rotating sleeve 2 mounted with a snapper bead 2a so that it can be rotated but can not be moved axially. Mounted on the external face of the guide sleeve 3 is the dose setting knob 1 which can likewise be rotated by virtue of a snapper bead 3a but can not be moved axially. Disposed at the proximal end of the rotating sleeve 2 and connected to the guide sleeve 3 and rotating sleeve 2 is a spring element 4, which, in one preferred embodiment, is provided in the form of a two to three-times coiled spring wire or spring strip. A rotation of the rotating sleeve 2 relative to the guide sleeve 3 tenses the spring 4, which is attached by bends 4a at the opposite ends to the guide sleeve 3 on the one hand and to the rotating sleeve 2 on the other hand, thereby producing a return force opposing the setting rotating movement.

In some preferred embodiments, the dose setting knob 1 is not pulled out axially but rotated. Disposed on the internal face of the dose setting knob 1 pointing in the axial direction are four webs. The webs engage in matching grooves of the rotating sleeve 2 and couple the dose setting knob 1 with the rotating sleeve 2. Thus, a rotating movement of the dose setting knob 1 can be transmitted to produce a rotating movement of the rotating sleeve 2. In principle, the dose setting knob 1 and rotating sleeve 2 could be of an integral design or provided as one element.

Figure 5:
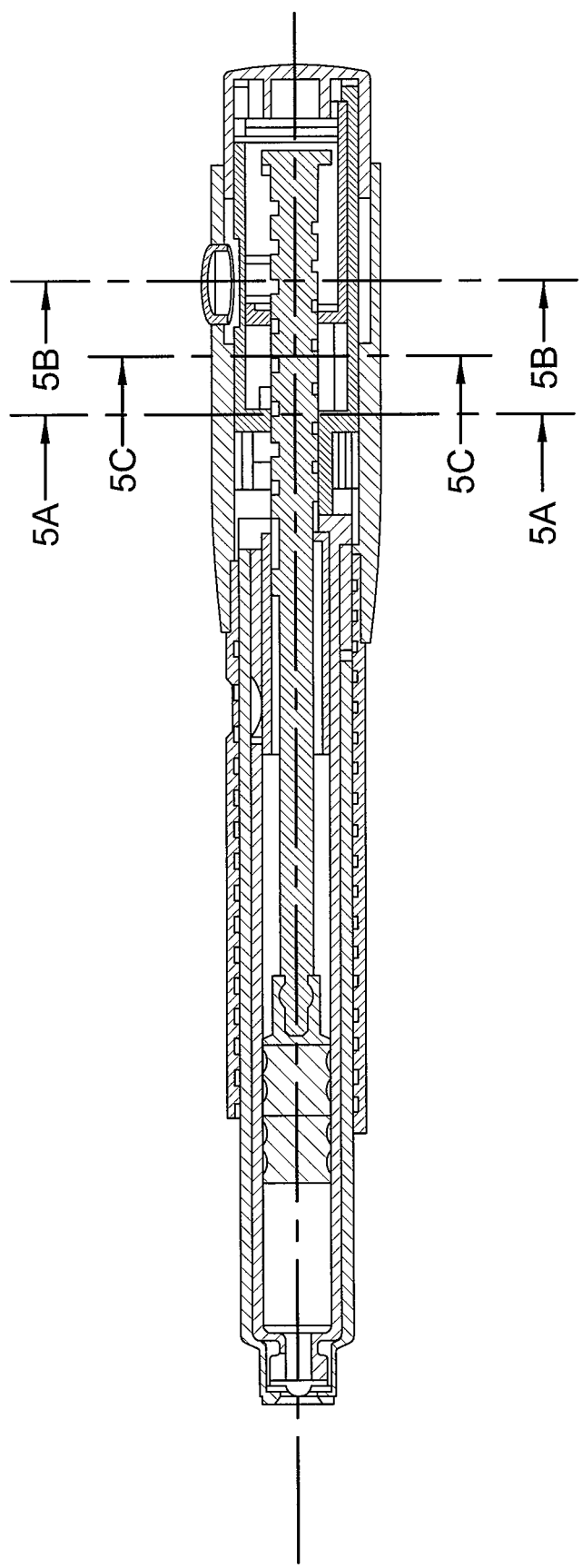
FIG. 5 shows the injection device illustrated in FIG. 4 after setting the dose and tensioning the spring.
Figure 5A:
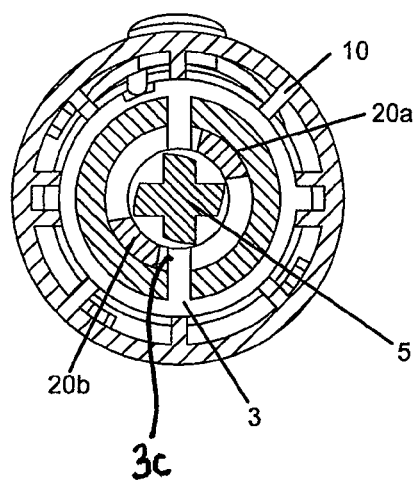
Figure 5B:
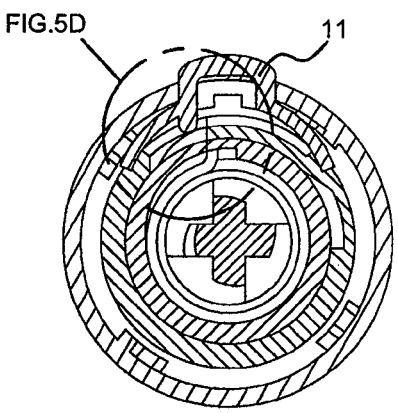
Figure 5C:
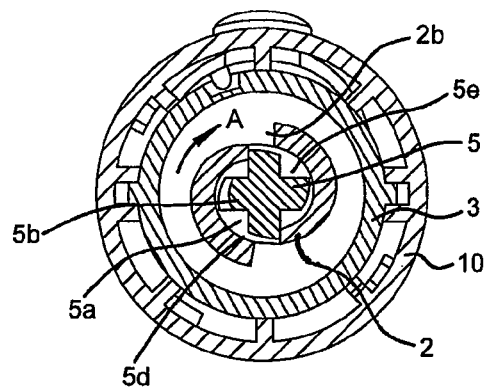
Figure 5D:
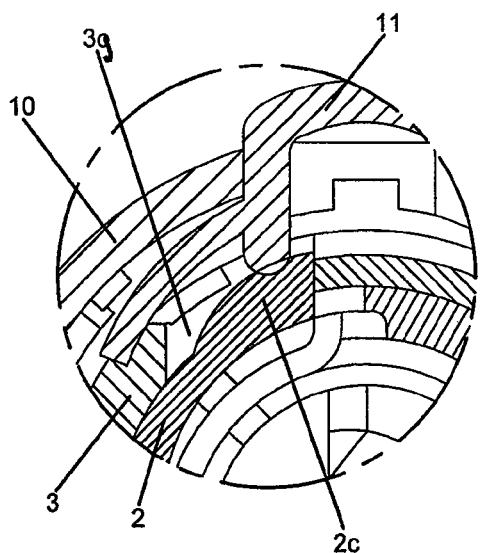
Figure 6:
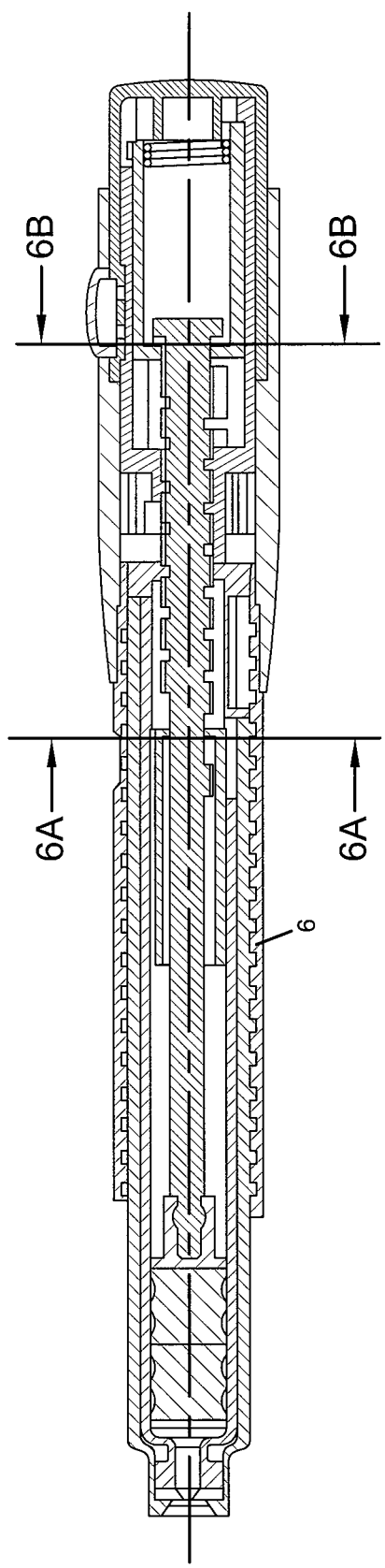
FIG. 6 shows the injection device illustrated in FIG. 5 after dispensing the dose with the mechanism blocked and the spring relaxed.
Figure 6B:
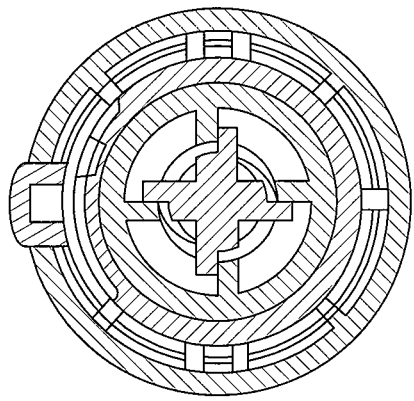
Figure 6A:
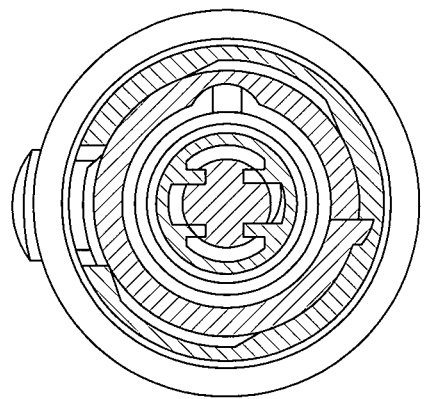
Figures 10A, 10B:
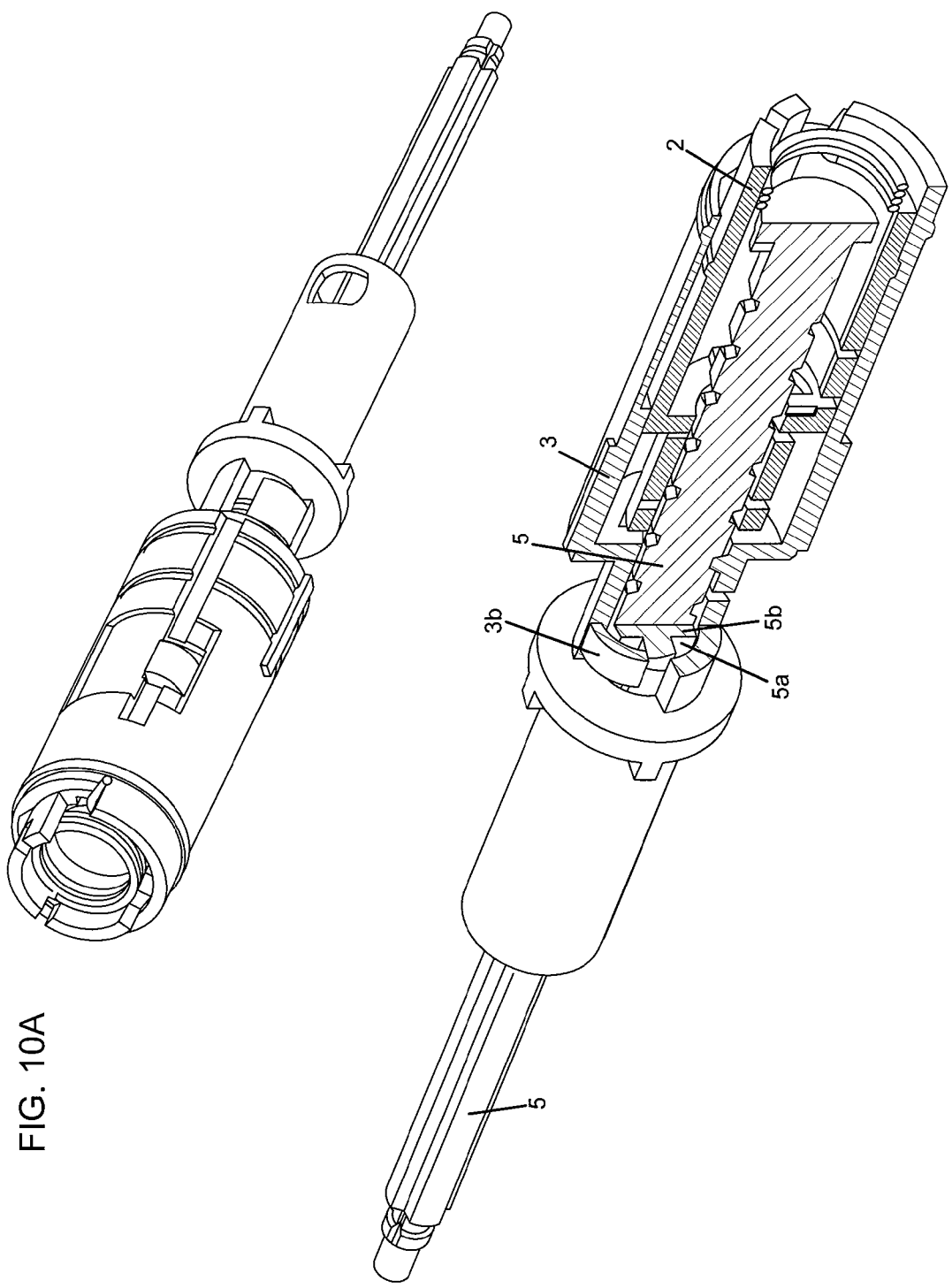
FIG. 10A is a perspective view illustrating an embodiment of a dose setting mechanism of an injection device in accordance with the present invention.
FIG. 10B shows the dose setting mechanism illustrated in FIG. 10A with a cross-sectional view of the proximal part.

The rotating sleeve 2 has snapper elements 2b pre-tensioned radially inwardly and, in the embodiment illustrated as an example in section C-C in FIG. 5 and shown in FIG. 5C, has two oppositely lying snapper elements 2b pre-tensioned radially inwardly. These snapper elements 2b engage in the grooves 5a of the threaded rod 5 during the priming movement or are rotated past the points 5b. During the priming operation, the threaded rod 5 is mounted so that it can not rotate because it is retained by a snapper element 3b of the guide sleeve 3. The rotating sleeve 2 has a snapper element 2c pre-tensioned radially outwardly, which is rotated into a window or orifice 3g of the guide sleeve 3 illustrated in the section B-B shown in FIG. 5, and detail D in FIGS. 5B and D. Element 2c latches in the window 3g so that it is not possible for the rotating sleeve 2 to be turned back relative to and inside the guide sleeve 3 due to the force of the spring 4 tensioned by the setting operation. When the release button 11 of the pen lying above the window 3g of the guide sleeve 3 is depressed, the snapper element 2c of the rotating sleeve 2 is pushed out of the window 3c of the guide sleeve 3 and thus releases the rotating sleeve 2 from the guide sleeve 3 so that it can be turned back by the setting distance due to the force of the pre-tensioned torsion spring 4.

Provided on the distal end of the rotating sleeve 2 lying opposite one another in the circumferential direction are two stops, webs or cams 20a, 20b projecting in the axial direction, which permit a maximum rotation of the rotating sleeve 2 of approximately 110° because these cams move into abutment with cams 3c of the guide sleeve 3 which are also in the radial direction but oriented in the proximal direction.

When rotated back in the dispensing direction indicated by arrow A in the section C-C shown in FIG. 5, the snapper elements 2b of the rotating sleeve 2 pre-tensioned radially inwardly latch in the grooves 5a of the threaded rod 5 extending in the axial direction so that the threaded rod 5 is driven by the backward rotating movement of the rotating sleeve 2 and is thus screwed into the pen in the distal direction guided by an internal thread 3d of the guide sleeve 3. This causes a forward movement of the stopper or stoppers 13a, 13b of the ampoule 13 due to the ram 8 provided on the distal end of the threaded rod 5 or an extension element 5v connected to it into the ampoule 13, thereby dispensing the substance 13c contained in the ampoule 13. After dispensing, the pen can be primed again by rotating the dose setting knob 1 and the same dose can then be dispensed.

The threaded rod 5 can be made by an injection moulding process with two mould halves if the threaded rod 5 is based on a cross-section in the form of a simple cross. In the axial direction of the threaded rod 5, the grooves 5a in which the snappers 2b of the guide sleeve 2 engage may be continuous and thus interrupt the thread 5c on the external face of the threaded rod 5. This enables high or steep faces to be produced for the snapper 2b.

The outer or peripheral regions of the threaded rod 5 have a ramp 5d so that the snappers 2b can slide over and away more easily during priming. This also results in a higher face 5e on the side of the groove 5a of the threaded rod 5 extending in the axial direction, in which the snapper 2b engages, reliably preventing the rotating sleeve 2 from being turned back relative to the threaded rod 5.

In principle, with such a design of the threaded rod 5, it is easily possible to vary the thread pitch during the manufacturing process so that different quantities of dose to be dispensed can be set by the same setting rotating movement of 110° for example, depending on the respective pitch specifically available. In this respect, the internal thread 3d of the guide sleeve 3 can be changed so that it matches the modified pitch of the external thread 5c of the threaded rod 5. Alternatively, another option would be for the internal thread 3d of the guide sleeve 3 to be designed to guide different pitches of the external thread 5c of the rod 5 within a range of a minimum pitch predefined by the internal thread 3d up to a maximum pitch predefined by the internal thread 3d. FIG. 9 shows a single thread of the internal thread 3d of the guide sleeve 3 opened out with a minimum and a maximum pitch resulting from contact edges 3e and 3f of the internal thread 3d.

To ensure that the pen can not be primed again once the last dose has been dispensed, a claw lock is provided on the threaded rod 5. It has a wider region 5f at the proximal end of the threaded rod 5 from which four webs 5g project pointing distally in the axial direction, which move or are pushed into matching co-operating stops 2g of the rotating sleeve 2 after the last dose has been dispensed. As result, the threaded rod 5 is moved axially so far into the rotating sleeve 2 that the claws or webs 5g of the threaded rod 5 lie against matching co-operating stops 2g of the rotating sleeve 2. The webs of the claw lock are able to move into the corresponding co-operating stops 2g because when the injection device is operated, they are lightly or partially mechanically deformed or compressed and relax on reaching the end position, for example, and move into the co-operating stops provided in the form of recesses. The claws of the claw lock may also be resiliently mounted. When the injection device is operated, the resiliently mounted claws 5g slide along the co-operating stop 2g as illustrated in FIG. 12A and are deflected out in the direction indicated by the arrow. Once the dose has been dispensed, the claws 5g snap into the co-operating stop 2g as illustrated in FIG. 12B, so that the injection device can no longer be primed. Irrespective of the design of the claw lock 5g and the co-operating stops 2g, the system of the claw lock 5g and co-operating stops 2g in accordance with the present invention means that when the last dose has been dispensed, the pen can no longer be primed because the threaded rod is retained by the positive connection between the claw lock 5g and co-operating stops 21g so that it can not rotate. It is no longer possible to set another dose on the pen because the threaded rod 5 is mounted so that it can not rotate in the guide sleeve 3, and the dose setting knob 1 and the rotating sleeve 2 are prevented from rotating by the claw coupling 2g, 5g.

In some embodiments, a two-chamber ampoule 13 may be inserted or screwed into the injection device. For mixing purposes, the ampoule 13 is screwed into the pen, and once the ampoule 13 has been screwed far enough into the pen, it moves into abutment with the guide sleeve 3 and pushes it together with the dose setting knob 1 in the proximal direction of the pen. This causes the dose setting knob 1 to be pushed out of the pen and it is not until then that the pen can actually be set or primed.

Figure 13A:
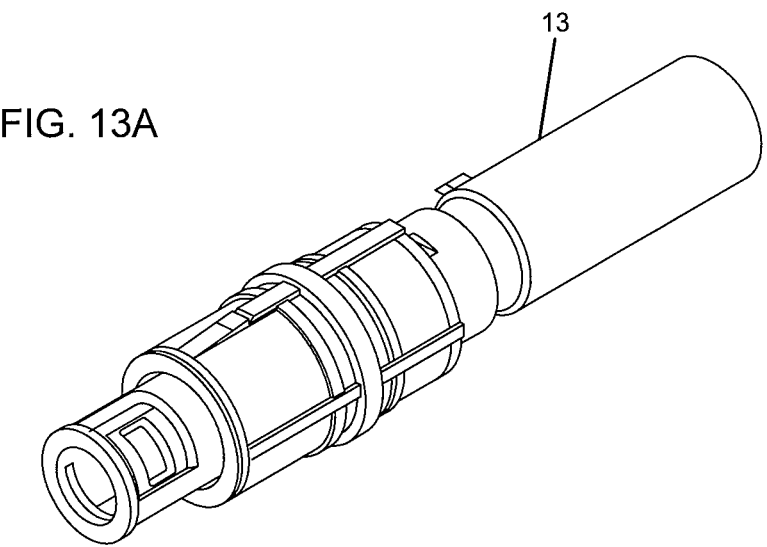
FIGS. 13A-13G show an embodiment of a mechanical lock in accordance with the present invention.
Figure 13B:
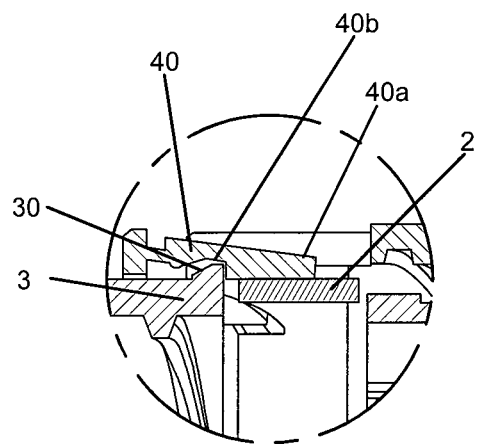
Figure 13C:
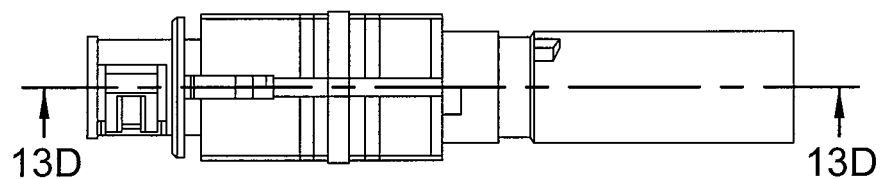
Figure 13D:
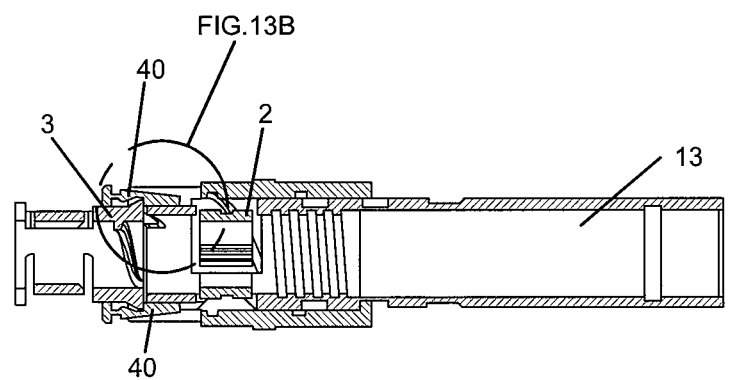

As illustrated in FIGS. 13B and 13C and the detailed view of FIG. 13D, a catch ring 40 or locking ring may be provided, for example, the two fork-shaped catch pawls 40a of which project into co-operating recesses of the rotating sleeve 2 and prevent the rotating sleeve 2 from rotating. Since the injection device is charged by rotating the rotating sleeve 2, the injection device is prevented from being primed or charged due to the engagement of the catch ring 40 in the rotating sleeve 2.

Figure 13E:
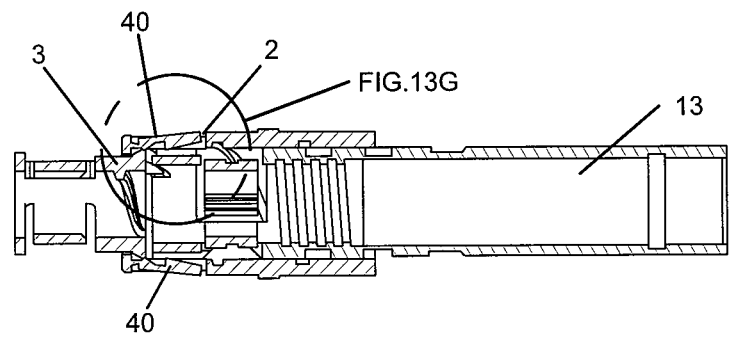
Figure 13F:
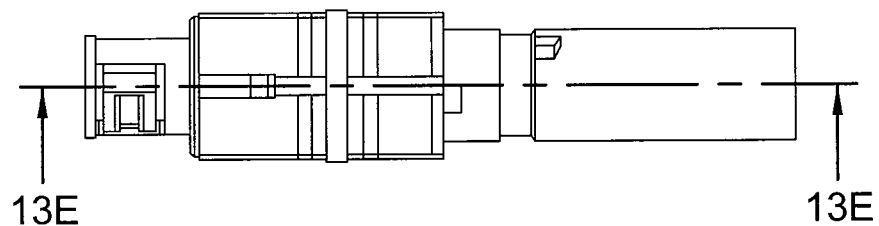
Figure 13G:
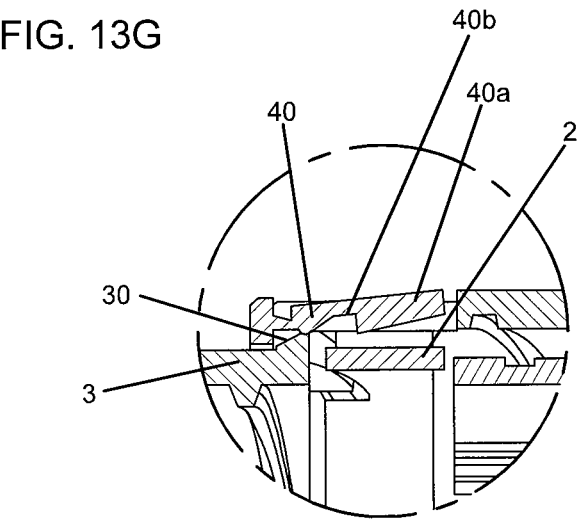

To release the catch ring 40 and the rotating sleeve 2, the ampoule sleeve which is screwed into the pen to mix the two-chamber ampoule is screwed in. In the last millimetres of movement, such as the last 1 to 3 mm, for example approximately the last 2 millimetres, the catch ring 40 is moved by the ampoule sleeve from the locked position into a released position in which the catch ring 40 is no longer latched to the rotating sleeve 2. Once the ampoule 13 has been screwed in far enough, the two catch pawls 40 of the catch ring or locking ring 40 are pushed out, as illustrated in FIGS. 13E to 13G, whereby oblique surfaces 40b or sliding surfaces disposed on the internal faces of the two fork-shaped catch pawls 40a slide relative to and along oblique surfaces 30 or sliding surfaces formed on the guide sleeve 3. Thus, the catch ring 40 is moved out of engagement with the rotating sleeve 2 and the rotating sleeve 2 is released so that it can effect rotating movements, for example to enable a dose to be set.

A display sleeve 6 is also provided on or associated with the threaded rod 5, which is fixedly connected to the threaded rod, i.e. fixed in rotation and axially displaceable. On the external face of the display sleeve 6, the dose quantities still to be dispensed are displayed in the circumferential direction. A viewing window 12 made from transparent materials or orifices 12.3, 12.9, 12.7 may be provided in the guide sleeve 3, ampoule holder 9 and threaded sleeve 7 (from the inside towards the outside).

When the ampoule 13 has been mixed, the display sleeve 6 is pushed into it (but not before). In principle, the display sleeve 6 could also be mounted on the rear stopper 13a so that it can rotate, in which case the display sleeve 6 is initially uncoupled from the mechanical system of the pen and is provided in the ampoule part.

Since there is a direct coupling between the display sleeve 6 and the threaded rod 5, the display sleeve 6 is not able to slip. This means that an incorrect display is not possible, even if the pen is dropped and subjected to a strong impact, for example.

The guide sleeve 3 is also used as a visual screen because the window 12.3 in the guide sleeve 3 is offset from the window 12.7 in the threaded sleeve 7 before the ampoule 13 is screwed in. Only after screwing in and mixing the ampoule 13 is the window 12.3 of the guide sleeve 3 moved to a position congruent with the window 12.7 of the threaded sleeve 7 so that the display sleeve 6 mounted on the threaded rod 5 becomes visible as a result and can be read.

The release button 11 is positioned in a hole in the housing 10 and has two resilient arms 11a in the circumferential direction, which push the releaser button 11 radially outwardly away from the guide sleeve 3. The resilient arms 11a describe a radius which is smaller than the external radius of the guide sleeve 3 to enable the release button 11 to be pretensioned radially outwardly.

Figure 11A:
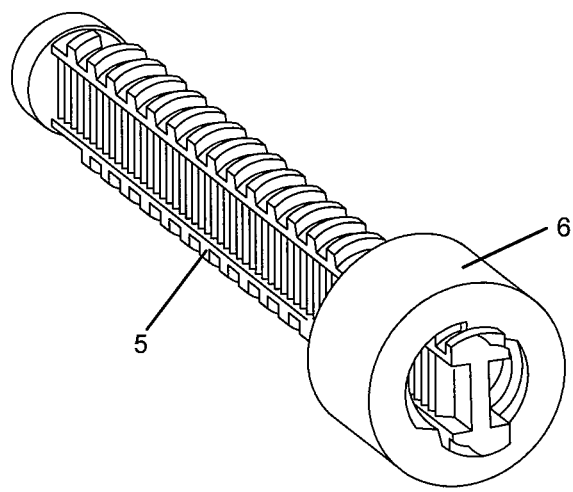
FIGS. 11A-11C show different embodiments of a real-time or remaining quantity display.
Figure 11B:
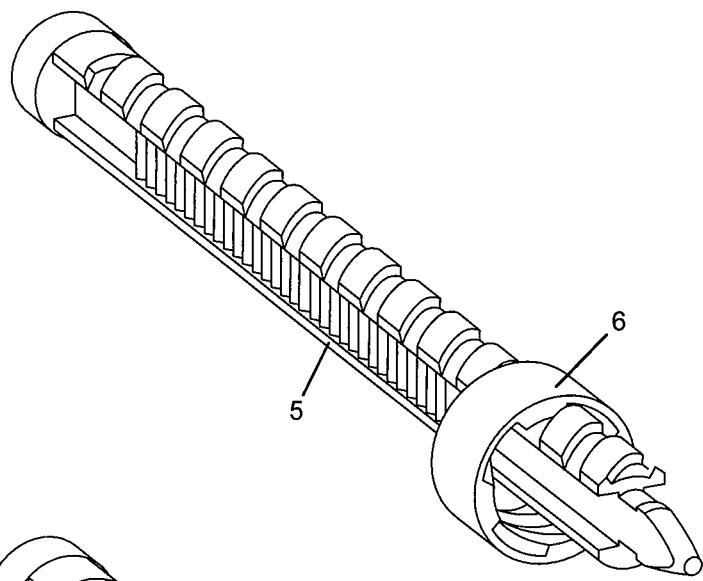

The display 6 is directly coupled with the plunger rod or threaded rod 5 in the embodiments illustrated in FIGS. 11A and 11B and can be rotated about it without being retained by friction.

Figure 11C:
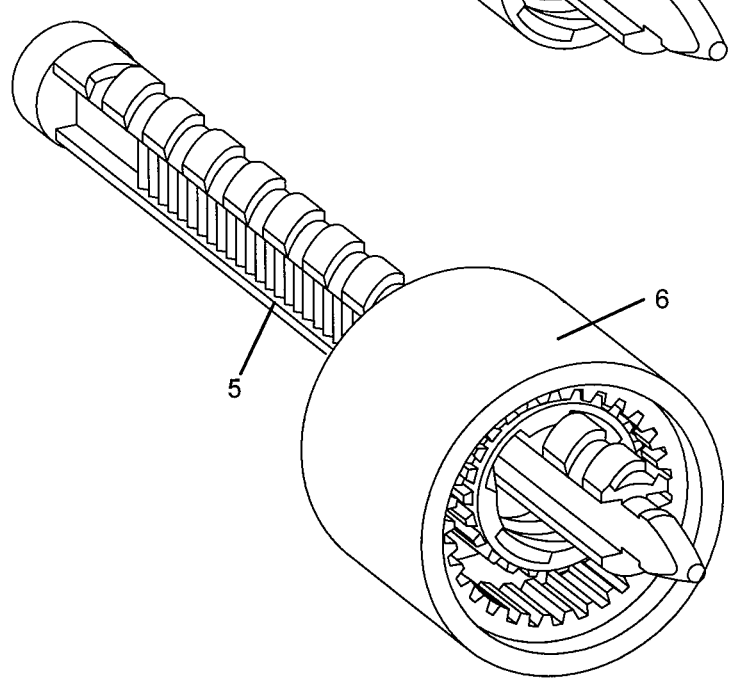

The plunger rod 5 has a thread or threaded part on the external face, in which the display 6 or, if a transmission is used for the display 6, transmission element coupled with the display 6, for example a gear or a gear with an internal thread as illustrated in FIG. 11C, can engage. If a transmission is used, a gap is formed between the gear directly coupled with the toothed rack and the display, through which the guide sleeve 3 can be inserted, for example.

If, instead of the toothed rack, a rotating mechanism is used with a plunger rod, the remaining quantity display can also be used. To this end, the remaining quantity display element 6 could be mounted so that it can not rotate on the plunger rod 5 so that, when dispensing, the plunger rod 5 is moved by the remaining quantity display 6 which is in turn mounted in the pen so that it is not able to move axially.

A remaining quantity display 6 which is not retained by friction can be achieved by using an appropriate thread pitch, which is dependent on the material and is approximately 45° in the embodiment illustrated as an example here.

The coupling between the remaining quantity display element 6 and toothed rack 5 is designed so that when the toothed rack 5 is fully inserted, the remaining quantity display element has effected a full rotation of 360°. In the event of a rotation of >360°, the display element 6 may be designed so that it can be moved farther by the external thread.

It would also be conceivable to use an axially displaceable remaining quantity display 6, which moves axially relative to the injection device as the toothed rack 5 is moved, for example by a thread engagement on the external face of the remaining quantity display 6 in an internal thread in the housing of the device. For example, an injection pen with a constant, pre-set dose may be used and the remaining quantity display shows 14 maximum possible units to be dispensed, which can be counted back to 0 starting from an initial state.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising:
   a rotating sleeve having an inner surface and engaging elements formed on the inner surface of the sleeve;
   a guide sleeve having an inner surface on which an internal thread is provided, said internal thread having an outer contact surface including at least two contact faces, each contact face having a different pitch angle to enable threaded engagement of the internal thread with a selected one of a plurality of threaded rods each having a thread with a different pitch angle; and
   the selected one threaded rod positioned within the rotating sleeve and the guide sleeve, wherein the threaded rod comprises a selected pitch angle and is engaged with the internal thread of the guide sleeve;
   wherein the threaded rod is rotatable relative to the injection device in a first circumferential direction and not rotatable relative to the injection device in a second circumferential direction;
   wherein the rotating sleeve rotates in a priming movement in the second circumferential direction to charge a dose and releasably engages the threaded rod by the engaging elements;
   wherein the primed rotating sleeve rotates in the first circumferential direction, and via an engagement of the engaging elements with the threaded rod, the rotating sleeve rotates the threaded rod with it and the threaded rod is driven to deliver the charged dose; and
   wherein upon dose delivery, the threaded rod is held at one of a plurality of selected stable positions.

2. The injection device according to claim 1, wherein the engaging elements releasably engage longitudinally extending grooves formed in the threaded rod to position the threaded rod into one of the selected stable positions.

3. The injection device according to claim 1, wherein the internal thread comprises at least two thread portions.

4. The injection device as claimed in the claim 3, wherein the thread portions are offset from one another.

5. The injection device as claimed in claim 3, wherein at least one of the thread portions has at least two parallel contact faces.

6. The injection device as claimed in claim 3, the thread portions have four contact faces and two of said contact faces are respectively parallel with one another.

7. The injection device according to claim 1, further comprising a display sleeve for providing a display of information related to the substance, wherein the display sleeve is coupled with the threaded rod such that the display sleeve is rotated upon displacement of the threaded rod and is axially displaceable with respect to the threaded rod.

8. The injection device according to claim 7, wherein the display sleeve is connected to the threaded rod directly.

9. The injection device according to claim 7, wherein the display sleeve is indirectly coupled with the threaded rod.

10. The injection device according to claim 9, wherein the display sleeve is indirectly coupled with the threaded rod by a thread engagement.

11. The injection device according to claim 1, further comprising a safety lock comprising co-operating webs and stops whereby, when a last dose has been dispensed, the device can no longer be primed because the threaded rod is retained by the co-operating webs and stops so that the threaded rod can not rotate.

12. The injection device according to claim 1, wherein the threaded rod comprises a plurality of longitudinally extending engagement grooves which one or more engaging elements of the rotating sleeve releasably engage when the threaded rod is in any of the plurality of stable positions.

13. The injection device according to claim 12, wherein the threaded rod is rotatable into four stable positions.

14. The injection device according to claim 12, wherein the engaging elements are radially pretensioned towards the threaded rod.

15. The injection device according to claim 14, wherein an outer surface region of the threaded rod extending circumferentially between each of the plurality of longitudinally extending engagement grooves defines a chamfered surface region.

16. The injection device according to claim 15, wherein rotation of the threaded rod in the first circumferential direction is achieved by sliding the engaging elements across the chamfered surface regions and rotation of the threaded rod in the second circumferential direction is blocked due to engagement of the engaging elements into the longitudinally extending engagement grooves.

17. The injection device according to claim 1, wherein the internal thread comprises at least two thread segments and wherein the threaded segments are offset from one another in a circumferential direction.

18. The injection device according to claim 1, further comprising a spring connected to the guide sleeve and the rotating sleeve, wherein the spring is tensed as the rotating sleeve rotates in the priming movement, and the tensed spring forces the rotating sleeve in rotation in the first circumferential direction.

19. The injection device according to claim 18, further comprising a release button, wherein the rotating sleeve comprises a snapper element radially pretensioned outwards, whereby when the rotating sleeve rotates in the priming movement, the snapper element latches outwards into a window of the guide sleeve and prevents the rotating sleeve from being turned in the first circumferential direction, and when the release button is actuated, the snapper element is pushed out of the window and the tensed spring rotates the rotating sleeve in the first circumferential direction.

20. The injection device according to claim 1, wherein the injection device is a fixed dose device in which the rotating sleeve rotates in the priming movement by a fixed charged dose and the threaded rod is driven to deliver the fixed charged dose.

21. The injection device according to claim 20, wherein the selected pitch angle corresponds to a selected fixed dose to be delivered.

22. The injection device according to claim 1, wherein the rotating sleeve comprises cams projecting axially relative to the injection device and the guide sleeve comprises cams, and wherein the rotating sleeve is maximally rotatable to a position in which the cams of the rotating sleeve and the guide sleeve abut.

23. The injection device according to claim 22, wherein the injection device is a fixed dose device in which abutment of the cams of the rotating sleeve and the guide sleeve corresponds to a fixed charged dose.

24. The injection device according to claim 23, wherein the selected pitch angle corresponds to a selected fixed dose to be delivered.

25. The injection device according to claim 1, wherein the rotating sleeve engaging elements are radially pretensioned towards the threaded rod.

26. The injection device according to claim 1, further comprising a release button, wherein the rotating sleeve comprises a snapper element radially pretensioned outwards, whereby when the rotating sleeve rotates in the priming movement, the snapper element latches outwards into a window of the guide sleeve and prevents the rotating sleeve from being turned in the first circumferential direction, and when the release button is actuated, the snapper element is pushed out of the window and the priming sleeve rotates in the first circumferential direction.

* * * * *